(12) United States Patent
Zhang et al.

(10) Patent No.: US 11,919,845 B2
(45) Date of Patent: Mar. 5, 2024

(54) REACTION SYSTEM AND METHOD FOR PREPARING BUTYRALDEHYDE BY PROPYLENE CARBONYLATION

(71) Applicant: NANJING INSTITUTE OF MICROINTERFACE TECHNOLOGY CO., LTD, Nanjing (CN)

(72) Inventors: Zhibing Zhang, Nanjing (CN); Zheng Zhou, Nanjing (CN); Lei Li, Nanjing (CN); Feng Zhang, Nanjing (CN); Weimin Meng, Nanjing (CN); Baorong Wang, Nanjing (CN); Gaodong Yang, Nanjing (CN); Huaxun Luo, Nanjing (CN); Guoqiang Yang, Nanjing (CN); Hongzhou Tian, Nanjing (CN); Yu Cao, Nanjing (CN); Jia Liu, Nanjing (CN)

(73) Assignee: NANJING INSTITUTE OF MICROINTERFACE TECHNOLOGY CO., LTD, Nanjing (CN)

( * ) Notice: Subject to any disclaimer, the term of this patent is extended or adjusted under 35 U.S.C. 154(b) by 0 days.

(21) Appl. No.: 18/276,252

(22) PCT Filed: Jul. 30, 2021

(86) PCT No.: PCT/CN2021/109748
§ 371 (c)(1),
(2) Date: Aug. 8, 2023

(87) PCT Pub. No.: WO2022/205717
PCT Pub. Date: Oct. 6, 2022

(65) Prior Publication Data
US 2024/0034707 A1   Feb. 1, 2024

(30) Foreign Application Priority Data
Apr. 1, 2021 (CN) .......................... 202110354339.1

(51) Int. Cl.
*C07C 45/50* (2006.01)

(52) U.S. Cl.
CPC .......... *C07C 45/50* (2013.01); *C07C 2523/46* (2013.01)

(58) Field of Classification Search
CPC ..... C07C 45/50; C07C 2523/46; C07C 29/17; C07C 31/125
See application file for complete search history.

(56) References Cited

FOREIGN PATENT DOCUMENTS

| CN | 112452268 A | 3/2021 |
|---|---|---|
| CN | 112479840 A | 3/2021 |

*Primary Examiner* — Jafar F Parsa
(74) *Attorney, Agent, or Firm* — Best & Flanagan LLP

(57) ABSTRACT

The invention provides a reaction system for preparing butyraldehyde by propylene carbonylation, comprising: a reactor; a side wall of the reactor is sequentially provided with a catalyst inlet, a propylene inlet and a synthesis gas inlet from top to bottom; the bottom of the reactor is provided with a solvent inlet; two micro-interface generators are arranged inside of the reactor from top to bottom, and the micro-interface generator located at a top end is connected to the propylene inlet to break the propylene gas into micron-scale micro-bubbles; the micro-interface generator located at a bottom is connected to the synthesis gas inlet for breaking the synthesis gas into micron-scale micro-bubbles; the outlets of the two micro-interface generators are opposite, and the outlets are connected with a gas distributor for evenly distributing raw materials. The reaction system of the present invention has low energy consumption, low cost, high safety, low reaction temperature and low reaction pressure, few side reactions and high yield of n-butyralde- (Continued)

hyde, which is worthy of wide popularization and application.

10 Claims, 2 Drawing Sheets

REACTION SYSTEM AND METHOD FOR PREPARING BUTYRALDEHYDE BY PROPYLENE CARBONYLATION

FIELD OF THE INVENTION

The present invention relates to the technical field of reaction preparation of propylene hydroxylation, in particular to a reaction system for preparing butyraldehyde by propylene carbonylation and a method thereof.

BACKGROUND OF THE INVENTION

Butyl octanol is an important raw material for the synthesis of fine chemical products, and the preparation of n-butyraldehyde is the most important part in the process of preparing butanol octanol, In the prior art, the generation of butyraldehyde mainly takes synthesis gas and propylene as raw materials, and the rhodium carbonyl/triphenylphosphine complex is used as a catalyst to react to generate mixed butyraldehyde, which is further rectified to obtain a butyraldehyde mixture after separating the catalyst. However, in the prior art, in the oxo reaction of synthesis gas and propylene under the action of a catalyst, the synthesis gas, propylene and catalyst cannot be fully mixed inside the oxo reactor, resulting in low reaction efficiency and high energy consumption during the reaction process. Because the reaction temperature is too high, the yield of n-butyraldehyde in the generated butyraldehyde mixture is low, the service life of the catalyst is short, and the production cost of the enterprise is increased.

In view of this, the present invention is proposed.

SUMMARY OF THE INVENTION

A first objective of the present invention is to provide a reaction system for preparing butyraldehyde by propylene carbonylation. On the one hand, the reaction system disperses and breaks the material into micro-bubbles by disposing a micro-interface generator inside the reactor, thereby increasing the phase boundary area between the gas-phase and the liquid-phase. Therefore, the mas transfer space is fully satisfied, the residence time of the gas in the liquid-phase is increased, the energy consumption is reduced, and reaction efficiency is improved. On the other hand, the operation temperature and the operation pressure inside the reactor are reduced, and the safety and stability of the entire reaction system are improved.

A second objective of the present invention is to provide a reaction method for preparing butyraldehyde using the above-mentioned reaction system for preparing butyraldehyde by propylene carbonylation. The reaction method is simple and convenient to operate, and the obtained n-butyraldehyde has high purity and high product quality, which is beneficial to reduce energy consumption, and achieves a better reaction effect than the existing process.

In order to realize the above-mentioned objectives of the present invention, the following technical schemes are specially adopted:

The present invention provides a reaction system for preparing butyraldehyde by propylene carbonylation, including; a reactor, a propylene storage tank, a carbon monoxide storage tank, a hydrogen storage tank, a propylene pipeline and a synthesis gas pipeline. The side wall of the reactor is provided with a catalyst inlet, a propylene inlet and a synthesis gas inlet sequentially from top to bottom, and the bottom of the reactor is provided with a solvent inlet.

The inside of the reactor is provided with two micro-interface generators from top to bottom, the micro-interface generator located at the top is connected with the propylene inlet to break the propylene gas into micron-scale micro-bubbles; the micro-interface generator located at the bottom is connected with the synthesis gas inlet for breaking the synthesis gas into micron-scale micro-bubbles; the outlets of the two-interface generators are opposite, and both the outlets are connected with a gas distributor for evenly distributing raw materials.

The carbon monoxide storage tank is connected in parallel with the hydrogen storage tank, and both the carbon monoxide storage tank and the hydrogen storage tank are connected to the synthesis gas inlet through the synthesis gas pipeline; both the propylene pipeline and the synthesis gas pipeline are provided with bubble generators for pre-dispersing and breaking the gas into bubbles.

In the prior art, the generation of butyraldehyde mainly takes synthesis gas and propylene as raw materials, and it uses carbonyl rhodium/triphenylphosphine complex as a catalyst to generate a mixed butyraldehyde. After the catalyst is separated from the mixed butyraldehyde, further rectification is performed to obtain a butyraldehyde mixture, and then the butyraldehyde mixture is subjected to isomer separation to obtain n-butyraldehyde. However, in the prior art, during the carbonylation reaction process performed by synthesis gas and propylene under the action of a catalyst, the synthesis gas, propylene and catalyst cannot be fully mixed inside the oxo reactor, resulting in low reaction efficiency and high energy consumption during the reaction process, and the yield of n-butyraldehyde in the butyraldehyde mixture is low, which increases the production cost of the enterprise.

In order to solve the above-mentioned technical problems, the invention provides a reaction system for preparing butyraldehyde by propylene carbonylation. The reaction system disperses and breaks propylene and synthesis gas by disposing two micro-interface generators inside the reactor, which improves the mass transfer effect, greatly increases the mass transfer rate, and reduces the required reaction temperature and reaction pressure. By making the two-micro-interface generators face each other, the propylene micro-bubbles and synthesis gas micro-bubbles can have a hedging effect to realize the uniform distribution of the micro-bubbles. By disposing a gas distributor at the outlet of the micro-interface generators, the micro-bubbles are further distributed evenly. By disposing the bubble generator, the raw material gas is pre-broken, and the gas is broken into large bubbles before the gas is dispersed into micro-bubbles, and the micro-interface generators breaks these large bubbles into micro-bubbles, which improves the generation efficiency of the micro-bubbles.

It should be noted that, when the micro-interface generators are disposed in the present invention, the upper micro-interface generator is connected to the propylene inlet, and the lower micro-interface generator is connected to the synthesis gas inlet. Relatively speaking, the gas source of synthesis gas needs to be synthesized in advance, and the raw materials are all flammable and explosive gases. Hence, in order to improve its safety, try to dispose the position of its air inlet as low as possible. At the same time, in view of the fact that it is easier to flow towards the top of the reactor after it enters the reactor, the micro-interface generator for breaking propylene is disposed at the top, and the micro-interface generator for breaking synthesis gas is disposed at the bottom, such an arrangement also fully considers various factors such as safety and reaction efficiency. After the synthesis gas is fully broken and dispersed by the micro-interface generator, it will also pass through the gas distributor located on the top of the micro-interface generator with a higher probability to achieve a more uniform distribution.

Preferably, the gas distributor includes a distributor body and a plurality of nozzles; and the plurality of nozzles are obliquely arranged on the distributor body to uniformly disperse the micro-bubbles generated by the micro-interface generator. The purpose of the oblique arrangement is also to make the bubbles more dispersed, and the dispersed tile area is larger and more dispersed, thereby further improving the reaction efficiency.

The gas distributors are arranged at the gas outlets of each micro-interface generator to ensure that all the micro-interface generators seamlessly enter the distributor body and are sprayed out through the plurality of nozzles.

In the present invention, the micro-interface generators and the gas distributor are used in cooperation to ensure the dispersion and crushing of the gas, and at the same time, to improve the utilization rate of each micro-bubble through gas distribution, and to avoid the disordered state of the micro-bubbles from being unfavorable to the smooth progress of the reaction. In particular, the disposition positions of the micro-interface generators and the connection and arrangement of the gas distributors have been obtained through a lot of practice.

Preferably, the bubble generator includes a gas-phase main channel and a liquid-phase branch channel. The liquid-phase branch channel is connected to the reactor, and the solvent in the reactor enters the gas-phase main channel through the liquid-phase branch channel and mixes with the gas in the gas-phase main channel to form bubbles.

Preferably, a catalyst inlet is disposed on the side wall of the reactor, and a sprayer is disposed in the reactor. The sprayer is located above the micro-interface generator; the sprayer is connected to the catalyst inlet; and the catalyst inlet is connected with a catalyst storage tank. The catalyst is sprayed through the sprayer, which improves the reaction effect and makes the catalyst distribution more uniform.

In the present invention, two micro-interface generators are disposed in the reactor, which are respectively connected to the propylene inlet and the synthesis gas inlet. During the reaction, the reactor is first filled with solvent, so that the two micro-interface generators are immersed in the solvent, the propylene is dispersed and broken into large propylene bubbles in the bubble generator, and the large propylene bubbles enter into the micro-interface generator through the propylene inlet. The micro-interface generator further disperses and breaks into micron-scale micro-bubbles. At the same time, the synthesis gas is dispersed and broken into large synthesis gas bubbles in the bubble generator, and the large synthesis gas bubbles enter the micro-interface generator through the synthesis gas inlet, and then is further dispersed and broken into micron-scale micro-bubbles in the micro-interface generator. The solvent provides a liquid-phase medium for the dispersion and crushing of propylene and synthesis gas. Propylene and synthesis gas are respectively subjected to a micro-interface generator, which improves the efficiency of dispersion and crushing. The outlets of the two micro-interface generators are facing each other, which can play a hedging effect to achieve uniform distribution of micro-bubbles.

In the present invention, a gas distributor is disposed at the outlet of the micro-interface generator, and the generated micro-bubbles are sprayed in different directions through the plurality of nozzles on the gas distributor, so that the running direction of the micro-bubbles is changed, and the micro-bubbles are distributed more evenly. I can be seen that, the present invention improves the application effect of the micro-interface generator itself by combining the application of the bubble generator, the micro-interface generator and the gas distributor.

Those skilled in the art can understand that the micro-interface generator used in the present invention has been embodied in the inventor's previous patents, such as patent applications with application numbers CN201610641119.6, CN201610641251.7, CN201710766435.0, CN106187660, and CN105903425A, and patents with patent numbers CN109437390A, CN205833127U and CN207581700U. In the previous patent application CN201610641119.6, the specific product structure and working principle of the micro-bubble generator (that is, the micro-interface generator) are introduced in detail. The application document records that "the micro-bubble generator includes a main body and a secondary crushing component, the main body has a cavity, the main body is provided with an inlet communicating with the cavity, and the opposite first end and second end of the cavity are open, wherein the cross-sectional area of the cavity decreases from the middle of the cavity to the first end and the second end of the cavity. The secondary crushing component is arranged on at least one of the first end and the second end of the cavity. A part of the secondary crushing component is disposed in the cavity, and an annular channel is formed between the secondary crushing component and the through holes opened at both the first end and the second end of the cavity. The micro-bubble generator also includes an air inlet pipe and a liquid inlet pipe. From the specific structure disclosed in the application document, it can be known that its specific working principle is: the liquid enters the micro-bubble generator tangentially through the liquid inlet pipe, rotates at ultra-high speed and cuts the gas, so that the gas bubbles are broken into micron-scale micro-bubbles, thereby the mass transfer area between the liquid-phase and the gas-phase is increased. The micro-bubble generator in this patent is a pneumatic micro-interface generator.

In addition, in the previous patent 201610641251.7, it records that the primary bubble breaker has a circulation liquid inlet, a circulation gas inlet, and a gas-liquid mixture outlet, while the secondary bubble breaker connects the feed port with the gas-liquid mixture outlet, which indicates that the bubble breaker needs to mix gas and liquid to enter. Furthermore, it can be seen from the following drawings that the primary bubble breaker mainly uses circulating fluid as power, so in fact, the primary bubble breaker belongs to the hydraulic micro-interface generator. The secondary bubble breaker simultaneously feeds the gas-liquid mixture into the elliptical rotating ball for rotation, so that the bubbles are broken during the rotation. Hence, the secondary bubble breaker is actually a gas-liquid linkage micro-interface generator. In fact, no matter a hydraulic micro-interface generator or a gas-liquid linkage micro-interface generator, which belongs to a specific form of a micro-interface generator. However, the micro-interface generator adopted in the present invention is not limited to the above-mentioned several forms. The specific structure of the bubble breaker described in the prior patents is only one of the forms that can be adopted by the micro-interface generator of the present invention.

In addition, in the previous patent 201710766435.0, it records that "the principle of the bubble breaker is using high-speed jet flow to achieve gas collision", and it also explains that "it can be used in micro-interface strengthening reactors to verify the correlation between the bubble breaker and the micro-interface generator". Moreover, there are relevant records for the specific structure of the bubble breaker in the prior patent CN106187660, specifically refer to paragraphs [0031]-[0041] in the description and the accompanying drawings, which have a detailed description of the specific working principles of the bubble breaker S-2. The top of the bubble breaker is the liquid-phase inlet, and the side of the bubble breaker is the gas-phase inlet. The entrainment power is provided by the liquid-phase coming in from the top, so as to achieve the effect of crushing into ultra-fine bubbles. It can also be seen from the drawings that the bubble breaker has a conical structure, and the diameter of the upper part is larger than that of the lower part, which also helps the liquid-phase to provide better entrainment power.

Since the micro-interface generator was just developed in the initial stages of the patent application, it was names micro-bubble generator ((CN201610641119.6) and bubble breaker (201710766435.0), etc. With the continuous improvement of technology, it was later renamed as micro-interface generator. Now the micro-interface generator in the present invention is equivalent to the previous micro-bubble generator, bubble breaker, etc., but their names are different. In summary, the micro-interface generator of the present invention belongs to the prior art.

Preferably, the top of the reactor is connected with a first condenser; the non-condensable gas outlet of the first condenser is connected with a combustion system, and the condensate outlet of the first condenser is connected with the reactor. The tail gas at the top of the reactor is condensed by the first condenser, and high-boiling substances such as n-butyraldehyde/isobutyraldehyde are condensed into liquids and returned to the reactor. Non-condensable gases such as nitrogen, hydrogen, propane, and carbon monoxide enter the combustion system for combustion and removal.

Preferably, a solvent inlet is disposed at the bottom of the reactor, and the solvent inlet is connected to a solvent storage tank. The solvent in the solvent storage tank flows into the reactor through the solvent inlet to provide a medium for the reaction. Further, the solvent is n-butyraldehyde or isobutyraldehyde.

Preferably, the reactor is provided with a product outlet, and the product outlet is connected with a demister. The demister is sequentially connected with a gas-liquid separator, an isomer separator tower and a rectification tower. The rectification tower is connected with a n-butyraldehyde storage tank. The demister captures the small liquid droplets entrained in the gas flow from the reactor and returns them to the reactor.

Preferably, a second condenser is disposed between the demister and the gas-liquid separator. The product defoamed by the demister is condensed by the second condenser and flows into the gas-liquid separator. The second condenser condenses the gas-phase product and flows into the gas-liquid separator.

Preferably, the gas-liquid separator is also connected with a third condenser, and the third condenser is connected with the micro-interface generator located at the top of the reactor. A part of the product separated by the gas-liquid separator directly flows into the isomer separation tower, and another part of the product flows back into the reactor after being condensed by the third condenser. Further, a circulation pump is disposed at the outlet of the gas-liquid separator, and the liquid-phase stream at the bottom of the gas-liquid separator enters the circulation pump to raise the pressure. A part of the material at the outlet of the circulation pump flows into the isomer separation tower as a crude product, and the other part is cooled by the third condenser to about 80° C. and returned to the micro-interface generator in the reactor to continue to participate in the reaction.

In addition, the present invention also provides a reaction method using the above-mentioned reaction system for preparing butyraldehyde by propylene carbonylation, including the following steps:

After dispersing and crushing propylene and synthesis gas through the micro-interface generators respectively, they are mixed with catalysts to carry out hydroxyl synthesis reaction, and then the crude product is obtained after defoaming and condensing gas-liquid separation. A separation of the crude product is performed to separate out n-butyraldehyde and isobutyraldehyde, and n-butyraldehyde is obtained after rectification and purification.

Preferably, the hydroxyl synthesis reaction temperature is 85-90° C., and the reaction pressure is 1.1-1.8 MPa. Preferably, the catalyst is a rhodium catalyst.

Specifically, the reaction method disperses and crushes the propylene and the synthesis gas by disposing micro-interface generators inside the reactor. Therefore, before the carbonylation reaction of the propylene and the synthesis gas, they are broken into micro-bubbles with a diameter greater than or equal to 1 μm and less than 1 mm, such that the mass transfer area of the phase boundary is increased, the solubility of propylene and synthesis gas in the solvent is increased, the reaction pressure is reduced, and the reaction efficient is improved.

The n-butanol product obtained by adopting the reaction method of the present invention has excellent quality and high yield. Moreover, the preparation method itself has low reaction temperature, greatly reduced pressure, and significantly reduced cost.

Compared with the prior art, the beneficial effects of the present invention include:
(1) The reaction system of the present invention disperses and crushes propylene and synthesis gas by disposing two micro-interface generators inside the reactor, which improves the mass transfer effect, greatly increases the mass transfer rate, and reduces the required temperature and pressure for the reaction.
(2) By making the two micro-interface generators face each other, the propylene micro-bubbles and the synthesis gas micro-bubbles can have a hedging effect, so as to realize the uniform distribution of the micro-bubbles.
(3) By disposing a gas distributor at the outlet of the micro-interface generator, the micro-bubbles are further uniformly distributed.
(4) By disposing a bubble generator, the raw material gas is pre-broken, and the gas is broken into large bubbles before the gas is dispersed into micro-bubbles, and the micro-interface generator breaks these large bubbles into micro-bubbles, which improves generation efficiency of the micro-bubbles.

BRIEF DESCRIPTION OF THE DRAWINGS

Various other advantages and benefits will become apparent to those of ordinary skill in the art upon reading the following detailed description of the preferred embodiments. The drawings are only for the purpose of illustrating preferred embodiments and are not to be considered as limiting the invention. Also, throughout the drawings, the same reference numerals are used to designate the same components. In the attached drawings.

DESCRIPTION OF THE PREFERRED EMBODIMENTS

Figure 1:
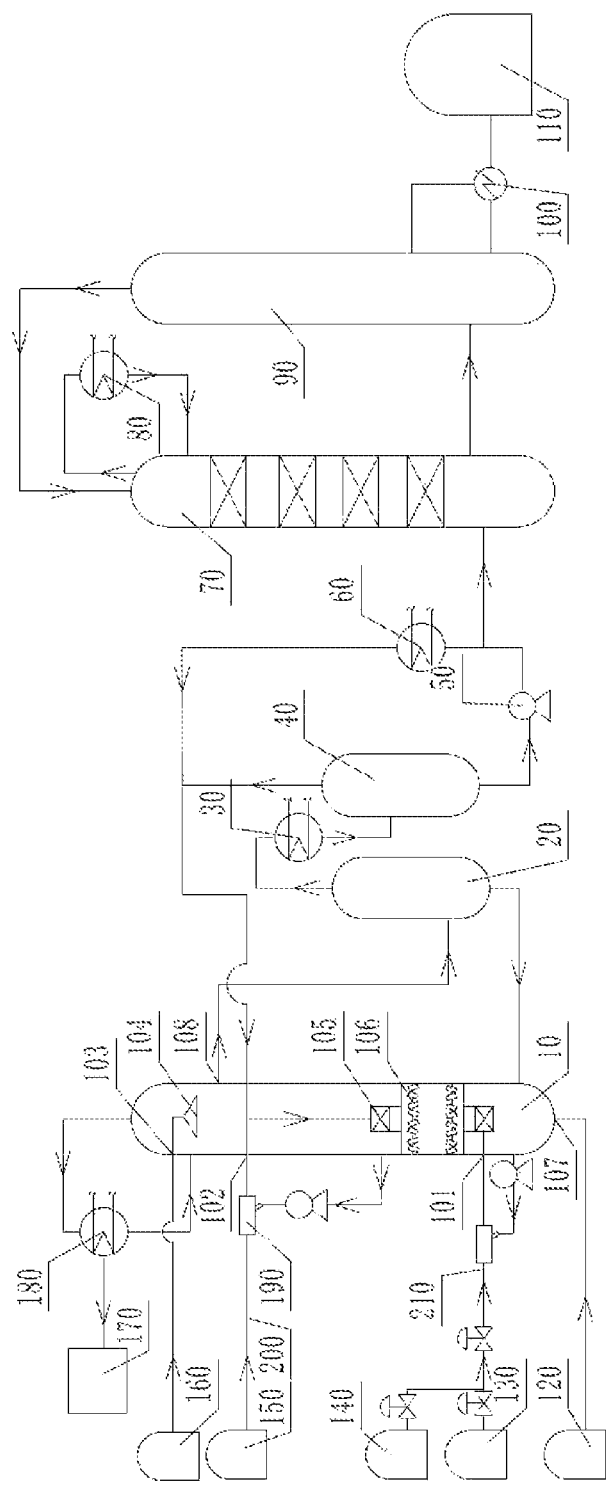
FIG. 1 is a structural diagram of a reaction system for preparing butyraldehyde by propylene carbonylation according to an embodiment of the present invention.

The technical schemes of the present invention will be clearly and completely described below in conjunction with the embodiments and the accompanying drawings. Those skilled in the art will understand that the following embodiments are some embodiments of the present invention, rather than all embodiments, and are only for illustrating the present invention, and should not be considered as limiting the scope of the present invention. Based on the embodiments of the present invention, all other embodiments obtained by persons of ordinary skill in the art without making creative efforts belong to the protection scope of the present invention. Those who do not indicate the specific conditions in the embodiments are carried or according to the conventional conditions or the conditions suggested by the manufacturer. The reagents or instruments used were not indicated by the manufacturer, and they were all conventional products that could be purchased from the market.

In the description of the present invention, it should be noted that the terms for indicating the orientation or positional relationship, such as "center", "upper", "lower", "left", "right", "vertical", "horizontal", "inner", "outer" etc. is based on the orientation or positional relationship shown in the drawings, and is only for the convenience of describing the present invention and simplifying the description; it is not intended to indicate or imply that the referred device or element must have a particular orientation, be constructed in a particular orientation, and operate in a particular orientation, and thus should be not construed as limiting the invention. In addition, the terms "first", "second", and "third" are used for descriptive purposed only, which should be not construed as indicating or implying relative importance.

In the description of the present invention, it should be noted that unless otherwise specified and limited, the terms "installed", "connection", "coupling" should be understood in a broad sense. For example, it can be a fixed connection, a detachable connection, or an integral connection; it can be a mechanical connection or an electrical connection; it can be a direct connection or an indirect connection through an intermediary, and it can be the internal connection between two components. Those of ordinary skill in the art can understand the specific meanings of the above items in the present invention in specific situations.

In order to illustrate the technical schemes in the present invention more clearly, the following will be described in the form of specific embodiments.

Embodiments

Figure 2:
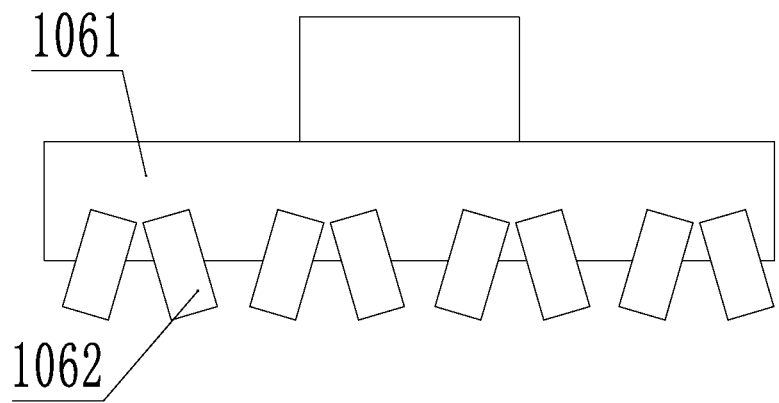
FIG. 2 is a structure diagram of a sprayer according to an embodiment of the present invention.
Figure 3:
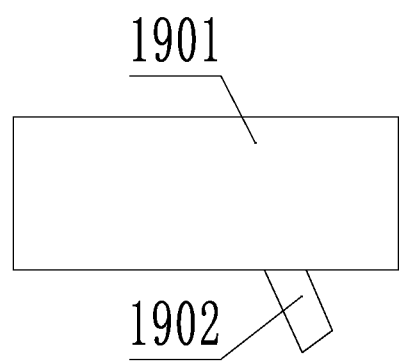
FIG. 3 is a structure diagram of a bubble generator according to an embodiment of the present invention.

Referring to FIG. 1 to FIG. 3, a reaction system for preparing butyraldehyde by propylene carbonylation is provided in this embodiment, which includes: a reactor 10, a propylene storage tank 150, a carbon monoxide storage tank 130, a hydrogen storage tank 140, a propylene pipeline 200 and a synthesis gas pipeline 210. The side wall of the reactor 10 is provided with a propylene inlet 102 and a synthesis gas inlet 101 sequentially from top to bottom.

The propylene inlet 102 is connected to the propylene storage tank 150 through the propylene pipeline 200; the carbon monoxide storage tank 130 is connected in parallel with the hydrogen storage tank 140, and both of them are connected to the synthesis gas inlet 101 through the synthesis gas pipeline 210. Both the propylene pipeline 200 and the synthesis gas pipeline 210 are provided with a bubble generator 190 for pre-dispersing and breaking the gas into bubbles.

As shown in FIG. 3, the bubble generator 190 includes a gas-phase main channel 1901 and a liquid-phase branch channel 1902; the liquid-phase branch channel 1902 is connected with the reactor 10, and the solvent in the reactor 10 enters the gas-phase main channel 1901 through the liquid-phase branch channel and mixes with the gas in the gas-phase main channel 1901 to form bubbles.

During the reaction, propylene enters the gas-phase main channel 1901 of the bubble generator 190 through the propylene pipeline 200, and the solvent in the reactor 10 enters the gas-phase main channel 1901 through the liquid-phase branch channel 1902, and mixes with the propylene in the gas-phase main channel 1901 to form propylene bubbles, the propylene bubbles and the remaining solvent flow back into the reactor 10 from the propylene inlet 102. At the same time, the synthesis gas enters the gas-phase main channel 1901 of the bubble generator 190 through the synthesis gas pipeline 210, and the solvent in the reactor 10 enters the gas-phase main channel 1901 through the liquid-phase branch channel 1902, and mixes with he synthesis gas in the gas-phase main channel 1901 to form synthesis gas bubbles, propylene bubbles and the remaining solvent flow back into the reactor 10 form the propylene inlet 102. A water pump is arranged at the inlet of the liquid-phase branch channel 1902 to pump the solvent to the liquid-phase branch channel 1902.

The interior of the reactor 10 is provided with two micro-interface generators 105 from top to bottom. The micro-interface generator 105 at the top is connected to the propylene inlet 102 to break the propylene gas into micron-scale micro-bubbles; and the micro-interface generator 105 at the bottom is connected to the synthesis gas inlet 101 for breaking the synthesis gas into micron-scale micro-bubbles. The outlets of the two micro-interface generators 105 are opposite, and both of the outlets are connected with gas distributors 106 for evenly distributing raw materials.

As shown in FIG. 2, the gas distributor 106 includes a distributor body 1061 and a plurality of nozzles 1062; the plurality of nozzles 1062 are obliquely arranged on the distributor body 1061 to uniformly disperse the microbubbles generated by the micro-interface generator 105.

A catalyst inlet 103 is arranged on the side wall of the reactor 10, and a sprayer 104 is also arranged in the reactor 10, wherein the sprayer 104 is located above the micro-interface generator 105. The sprayer 104 is connected with the catalyst inlet 103; and the catalyst inlet 103 is connected with a catalyst storage tank 160. During the reaction, the catalyst is sprayed by the sprayer 104 to make the catalyst distribution more uniform. The catalyst used in this embodiment is a rhodium catalyst.

A first condenser 180 is connected to the top of the reactor 10; a non-condensable gas outlet of the first condenser 180 is connected to the combustion system 170; and a condensate outlet of the first condenser 180 is connected to the reactor 10. The tail gas at the top of the reactor 10 is condensed by the first condenser 180, high boiling point substances such as n-butyraldehyde/Isobutyraldehyde are condensed into liquids and returned to the reactor 10, and non-condensable gases such as nitrogen, hydrogen, propane, and carbon monoxide enter the combustion system 170 for combustion remove.

A solvent inlet 107 is arranged at the bottom of the reactor 10, and the solvent inlet 107 is connected to a solvent storage tank 120. The solvent in the solvent storage tank 120 flows into the reactor 10 through the solvent inlet 107 to provide a medium for the reaction. In this embodiment, the selected solvent is n-butyraldehyde or Isobutyraldehyde.

In this embodiment, the reactor 10 is provided with a product outlet 108, and the product outlet 108 is connected with a demister 20. The demister 20 is connected with a gas-liquid separator 40, an isomer separation tower 70 and a rectification tower 90 in sequence. The rectification tower 90 is connected with a n-butyraldehyde storage tank 110. The demister 20 captures the small liquid droplets entrained in the gas flow from the reactor 10 and returns them to the reactor 10.

A fourth condenser 80 is arranged at the top of the isomer separation tower 70. Since the difference between the boiling points of n-butanol and isobutanol is small, a plurality of trays is arranged in the isomer separation tower 70 to increase the reflux.

Specifically, a second condenser 30 is provided between the demister 20 and the gas-liquid separator 40. The product demisted by the demister 20 is condensed by the second condenser 30 and flows into the gas-liquid separator 40. The second condenser 30 condenses the product in the gas-phase and flows into the gas-liquid separator 40.

In addition, the gas-liquid separator 40 is also connected with a third condenser 60, and the third condenser 60 is connected with the micro-interface generator 105 located at the top of the reactor 10. A part of the product separated by the gas-liquid separator 40 flows directly into the isomer separation tower 70, and another part of the product flows back into the reactor 10 after being condensed by the third condenser 60. Further, the outlet of the gas-liquid separator 40 is provided with a circulation pump 50, and the liquid-phase flow at the bottom of the gas-liquid separator 40 enters the circulation pump 50 to increase the pressure. A part of the material at the outlet of the circulation pump 50 flows into the isomer separation tower 70 as a crude product, and the other part is cooled by the third condenser 60 to about 80° C. and returned to the micro-interface generator 105 in the reactor 10 to continue to participate in the reaction.

The outlet of the rectification tower 90 is provided with a reboiler 100, and the reboiler 100 divides the stream flowing out from the rectification tower 90 into a gas-phase stream and a liquid-phase stream, wherein the gas-phase stream flows back to the rectification tower 90, and the liquid-phase stream flows into the n-butyraldehyde storage tank 110.

The specific reaction process of the reaction system of this embodiment is as follows:

Before the reaction, the reactor 10 is filled with a solvent, and the two micro-interface generators 105 are immersed in the solvent. During the reaction, propylene enters the bubble generator 190 through the propylene pipeline 200, disperses and breaks into large propylene bubbles under the participation of the solvent, and enters the micro-interface generator 105 through the propylene inlet 103, and the bubbles are further dispersed and broken into micron-scale micro-bubbles in the micro-interface generator 105. At the same time, carbon monoxide and hydrogen are mixed in the synthesis gas pipeline 210 for form the synthesis gas. The synthesis gas enters the bubble generator 190 through the synthesis gas pipeline 210, and it is dispersed and broken into large synthesis gas bubbles under the participation of the solvent. The large synthesis gas bubbles enter into the micro-interface generator 105 through the synthesis gas inlet 101, and then the large synthesis gas bubbles are further dispersed and broken into micron-scale micro-bubbles in the micro-interface generator 105. The catalyst is evenly sprayed into the solvent through the sprayer 104, and the generated micro-bubbles undergo carbonylation reaction in the solvent. The reaction product is defoamed by the demister 20 and then condensed by the second condenser 30 and flows into the gas-liquid separator 40. The gas-phase after the gas-liquid separation flows back into the reactor 10, a part of the liquid-phase enters the isomer separation tower 70, and the other part of the liquid-phase is cooled by the third condenser 60 to about 80° C. and returned to the micro-interface generator 105 in the reactor 10 to continue to participate in the reaction. The isomer separation tower 70 separates the products, and the separated n-butyraldehyde flows into the n-butyraldehyde storage tank 110 after being rectified in the rectification tower 90.

In a word, compared with the reaction system for preparing butyraldehyde by propylene carbonylation in the prior art, the reaction system of the present invention has low energy consumption, low cost, high safety, lower required reaction temperature and low reaction pressure, few side reactions, and high yield of n-butyraldehyde, so it is worthy of wide popularization and application.

Finally, it can be understood that the above Embodiments are merely exemplary implementations adopted to illustrate the principle of the present invention, but the present invention is not limited thereto. Although the present invention has been described in detail with reference to the foregoing embodiments, those skilled in the art should understand that: it can still modify the technical schemes described in the foregoing embodiments or perform equivalent replacements for some or all of the technical features. However, without departing from the principle and essence of the present invention, various modifications and improvements can be made, and these modifications and improvements are also regarded as the protection scope of the present invention.

What is claimed is:

1. A reaction system for preparing butyraldehyde by propylene carbonylation, characterized in that, comprising:
a reactor, a propylene storage tank, a carbon monoxide storage tank, a hydrogen storage tank, a propylene pipeline and a synthesis gas pipeline; a side wall of the reactor is sequentially provided with a propylene inlet and a synthesis gas inlet from top to bottom;
two micro-interface generators are arranged inside the reactor from top to bottom, and the micro-interface generator located at a top is connected with the propylene inlet to break the propylene gas into micron-scale micro-bubbles; the micro-interface generator located at a bottom is connected with the synthesis gas inlet for breaking the synthesis gas into micron-scale micro-bubbles; outlets of the two micro-interface generators are opposite, and the outlets are connected with a gas distributor for evenly distributing raw materials;
the propylene inlet is connected to the propylene storage tank through the propylene pipeline, the carbon monoxide storage tank is connected in parallel with the hydrogen storage tank, and both the carbon monoxide storage tank and the hydrogen storage tank are connected to the synthesis gas inlet through the synthesis gas pipeline; both the propylene pipeline and the synthesis gas pipeline are provided with bubble generators for pre-dispersing and breaking the gas into bubbles;

wherein the gas distributor comprises a distributor body and a plurality of nozzles; the plurality of nozzles is obliquely arranged on the distributor body for uniformly dispersing the micro-bubbles generated by the micro-interface generators;

wherein a catalyst inlet is arranged on the side wall of the reactor, and a sprayer is arranged in the reactor and the sprayer is located at a top of the micro-interface generator; the sprayer is connected to the catalyst inlet; and the catalyst inlet is connected with a catalyst storage tank.

2. The reaction system for preparing butyraldehyde by propylene carbonylation according to claim 1, wherein the bubble generator comprises a gas-phase main channel and a liquid-phase branch channel; the liquid-phase branch channel is connected to the reactor, and a solvent in the reactor enters the gas-phase main channel through the gas-phase branch channel through the liquid-phase branch channel for mixing with the gas in the gas-phase main channel to form bubbles.

3. The reaction system for preparing butyraldehyde by propylene carbonylation according to claim 1, wherein the top of the reactor is connected with a first condenser; a non-condensable gas outlet of the first condenser is connected with a combustion system, and a condensate outlet of the first condenser is connected with the reactor.

4. The reaction system for preparing butyraldehyde by propylene carbonylation according to claim 1, wherein a solvent inlet is arranged at the bottom of the reactor, and the solvent inlet is connected with a solvent storage tank.

5. The reaction system for preparing butyraldehyde by propylene carbonylation according to claim 1, wherein the reactor is provided with a product outlet, and the product outlet is connected with a demister; the demister is sequentially connected with a gas-liquid separator, an isomer separation tower and a rectification tower, and the rectification tower is connected with an n-butyraldehyde storage tank.

6. The reaction system for preparing butyraldehyde by propylene carbonylation according to claim 5, wherein the gas-liquid separator is connected with a third condenser, and the third condenser is connected with the micro-interface generator located at the top of the reactor; one part of the product separated by the gas-liquid separator directly flows into the isomer separation tower, and another part of the product flows back into the reactor after being condensed by the third condenser.

7. A reaction method using the reaction system for preparing butyraldehyde by propylene carbonylation according to claim 1, comprising the following steps:

after dispersing and crushing the propylene and the synthesis gas through the micro-interface generators, they are mixed with catalysts to carry out a hydroxyl synthesis reaction; and then a crude product is obtained after defoaming and condensing gas-liquid separation, a separation is performed on the crude product, such that n-butyraldehyde is separated from isobutyraldehyde, and n-butyraldehyde is obtained after rectification and purification.

8. The reaction method according to claim 7, wherein a reaction temperature of a hydroxyl synthesis is 85-90° C., and a reaction pressure is 1.1-1.8 Mpa.

9. The reaction method according to claim 7, wherein the catalyst is a rhodium catalyst.

10. The reaction system for preparing butyraldehyde by propylene carbonylation according to claim 5, wherein a second condenser is arranged between the demister and the gas-liquid separator; the product defoamed by the demister is condensed and flows into the demister through the second condenser in the gas-liquid separator.

* * * * *